(12) United States Patent
Ramakrishnan et al.

(10) Patent No.: US 12,420,045 B2
(45) Date of Patent: Sep. 23, 2025

(54) SYSTEM AND METHOD FOR PATIENT-VENTILATOR SYNCHRONIZATION/ONSET DETECTION UTILIZING TIME-FREQUENCY ANALYSIS OF EMG SIGNALS

(71) Applicant: GE Precision Healthcare LLC, Wauwatosa, WI (US)

(72) Inventors: Upasana Ramakrishnan, Chennai (IN); Sanketh Bhat, Bangalore (IN); Etika Agarwal, Bangalore (IN); Adnan Kutubuddin Bohori, Pune (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 863 days.

(21) Appl. No.: 17/695,585

(22) Filed: Mar. 15, 2022

(65) Prior Publication Data
US 2023/0293835 A1 Sep. 21, 2023

(51) Int. Cl.
*A61M 16/00* (2006.01)
*A61B 5/00* (2006.01)
(Continued)

(52) U.S. Cl.
CPC .......... *A61M 16/026* (2017.08); *G16H 40/63* (2018.01); *A61M 2230/08* (2013.01); *A61M 2230/60* (2013.01)

(58) Field of Classification Search
CPC .......... A61M 16/022–026; A61M 16/10–186; A61M 16/0057–0084; A61M 2230/60; A61B 5/313; A61B 5/389; A61B 5/397
See application file for complete search history.

(56) References Cited

U.S. PATENT DOCUMENTS 4,506,666 A 3/1985 Durkan
4,915,103 A 4/1990 Visveshwara et al.
(Continued)

FOREIGN PATENT DOCUMENTS

CA 2320816 C * 8/2009 ............ A61B 5/392
CN 106215295 A 12/2016
(Continued)

OTHER PUBLICATIONS

Chiti, Linda et al.; "Scalene muscle activity during progressive inspiratory loading under pressure support ventilation in normal humans", Respiratory Physiology & Neurobiology 164 (2008); pp. 441-448.
(Continued)

*Primary Examiner* — Kendra D Carter
*Assistant Examiner* — Mautin I Ashimiu
(74) *Attorney, Agent, or Firm* — Fletcher Yoder, P.C.

(57) ABSTRACT

A computer-implemented method for detecting onset of a spontaneous breath by a patient coupled to a ventilation system includes receiving, at a processor, an electromyography (EMG) signal from an EMG sensor disposed on the patient. The method also includes pre-conditioning, via the processor, the EMG signal to separate the EMG signal into a plurality of components having EMG information utilizing a set of bandpass filters. The method further includes individually analyzing, via the processor, each component of the plurality of components to detect an onset of the spontaneous breath by the patient. The method still further includes determining, via the processor, the onset of the spontaneous breath by the patient is occurring when at least two components of the plurality of components indicate the onset of the spontaneous breath by the patient.

17 Claims, 11 Drawing Sheets

(51) Int. Cl.
  *A61B 5/313* (2021.01)
  *A61B 5/389* (2021.01)
  *A61B 5/397* (2021.01)
  *A61M 16/12* (2006.01)
  *A61M 16/16* (2006.01)
  *A61M 16/22* (2006.01)
  *G16H 40/63* (2018.01)

(56) References Cited

U.S. PATENT DOCUMENTS

| | | |
|---|---|---|
| 5,024,228 A | 6/1991 | Goldstone et al. |
| 5,195,531 A | 3/1993 | Bennett |
| 5,520,192 A | 5/1996 | Kitney et al. |
| 5,755,674 A * | 5/1998 | Watson ............... A61B 5/332 600/595 |
| 5,820,560 A | 10/1998 | Sinderby et al. |
| 5,995,868 A | 11/1999 | Dorfmeister et al. |
| 6,317,627 B1 | 11/2001 | Ennen et al. |
| 6,397,845 B1 | 6/2002 | Burton |
| 6,411,843 B1 | 6/2002 | Zarychta |
| 6,431,171 B1 | 8/2002 | Burton |
| 6,588,423 B1 | 7/2003 | Sinderby |
| 6,837,241 B2 | 1/2005 | Samzelius |
| 6,920,878 B2 | 7/2005 | Sinderby et al. |
| 6,962,155 B1 | 11/2005 | Sinderby |
| 7,055,522 B2 | 6/2006 | Berthon-Jones |
| 7,100,609 B2 | 9/2006 | Berthon-Jones |
| 7,204,250 B1 | 4/2007 | Burton |
| 7,379,767 B2 | 5/2008 | Rea |
| 7,510,531 B2 | 3/2009 | Lee et al. |
| 7,575,005 B2 | 8/2009 | Mumford et al. |
| 7,640,055 B2 | 12/2009 | Geva et al. |
| RE41,291 E | 4/2010 | Viertio-Oja et al. |
| 7,809,433 B2 | 10/2010 | Keenan |
| 7,992,560 B2 | 8/2011 | Burton et al. |
| 8,028,694 B2 | 10/2011 | Hickle |
| 8,069,852 B2 | 12/2011 | Burton et al. |
| 8,109,269 B2 | 2/2012 | Eger |
| 8,280,498 B2 | 10/2012 | Jalde |
| 8,281,787 B2 | 10/2012 | Burton |
| 8,364,455 B2 | 1/2013 | Bloomberg et al. |
| 8,449,506 B2 | 5/2013 | Yang |
| 8,465,438 B2 | 6/2013 | Gumery et al. |
| 8,467,844 B2 | 6/2013 | Rea et al. |
| 8,469,026 B2 | 6/2013 | Bloomberg et al. |
| 8,577,477 B2 | 11/2013 | Thramann et al. |
| 8,597,184 B2 | 12/2013 | Addington et al. |
| 8,646,448 B2 | 2/2014 | Lagerborg et al. |
| 8,688,237 B2 | 4/2014 | Stanislaus et al. |
| 8,733,347 B2 | 5/2014 | Similowski et al. |
| 8,781,575 B2 | 7/2014 | de Vos et al. |
| 8,863,742 B2 | 10/2014 | Blomquist et al. |
| 8,897,867 B2 | 11/2014 | Heyer et al. |
| 8,932,199 B2 | 1/2015 | Berka et al. |
| 8,939,148 B2 | 1/2015 | Eger et al. |
| 9,005,122 B2 | 4/2015 | Addington et al. |
| 9,010,327 B2 | 4/2015 | Tiedje |
| 9,060,744 B2 | 6/2015 | Li |
| 9,060,794 B2 | 6/2015 | Kang et al. |
| 9,186,105 B2 | 11/2015 | Leininger et al. |
| 9,192,323 B2 | 11/2015 | Heyer et al. |
| 9,211,384 B2 | 12/2015 | Eger et al. |
| 9,238,114 B2 | 1/2016 | Eger et al. |
| 9,278,184 B2 | 3/2016 | Sofranko |
| 9,308,337 B2 | 4/2016 | Heyer et al. |
| 9,375,542 B2 | 6/2016 | Doyle et al. |
| 9,597,468 B2 | 3/2017 | Schindhelm et al. |
| 9,687,177 B2 | 6/2017 | Ramanan et al. |
| 9,776,005 B2 | 10/2017 | Meyyappan et al. |
| 9,839,241 B2 | 12/2017 | Davidson et al. |
| 9,901,251 B2 | 2/2018 | Grubis |
| 9,913,594 B2 | 3/2018 | Li et al. |
| 9,918,669 B2 | 3/2018 | Brown et al. |
| 9,931,079 B2 | 4/2018 | Li et al. |
| 9,949,661 B2 | 4/2018 | Eger et al. |
| 9,955,925 B2 | 5/2018 | Kannan et al. |
| 9,968,749 B2 | 5/2018 | Hansmann et al. |
| 10,058,669 B2 | 8/2018 | Razavi et al. |
| 10,117,676 B2 | 11/2018 | Pizolato |
| 10,136,859 B2 | 11/2018 | Cutaia |
| 10,390,733 B2 | 8/2019 | Toth et al. |
| 10,406,307 B2 | 9/2019 | Eger et al. |
| 10,610,652 B2 | 4/2020 | Zhang et al. |
| 10,722,669 B2 | 7/2020 | Reed |
| 2003/0000527 A1 | 1/2003 | Stenzler et al. |
| 2005/0124866 A1 | 6/2005 | Elaz et al. |
| 2005/0126578 A1 | 6/2005 | Garrison et al. |
| 2006/0020160 A1 | 1/2006 | Ito et al. |
| 2006/0254595 A1 | 11/2006 | Rea |
| 2006/0264762 A1 | 11/2006 | Starr |
| 2007/0173728 A1 | 7/2007 | Pu et al. |
| 2008/0257349 A1 | 10/2008 | Hedner et al. |
| 2009/0159082 A1 * | 6/2009 | Eger ................ A61M 16/026 128/204.23 |
| 2010/0249639 A1 | 9/2010 | Bhatt |
| 2011/0100366 A1 | 5/2011 | Chou |
| 2011/0108034 A1 | 5/2011 | Viertio-Oja |
| 2011/0257517 A1 | 10/2011 | Guttag et al. |
| 2012/0130205 A1 | 5/2012 | Burton et al. |
| 2012/0152249 A1 | 6/2012 | Eger et al. |
| 2013/0213399 A1 * | 8/2013 | Hansmann ........ A61M 16/024 128/204.23 |
| 2014/0283834 A1 * | 9/2014 | Ahmad ............ A61M 16/0006 128/204.23 |
| 2015/0105701 A1 | 4/2015 | Mayer et al. |
| 2016/0228661 A1 | 8/2016 | Larsson et al. |
| 2016/0262699 A1 | 9/2016 | Goldstone et al. |
| 2016/0303340 A1 | 10/2016 | Sinderby et al. |
| 2017/0007789 A1 | 1/2017 | Chou |
| 2017/0119984 A1 | 5/2017 | Bahns et al. |
| 2017/0128684 A1 | 5/2017 | Sinderby et al. |
| 2017/0224234 A1 | 8/2017 | Ahlmen et al. |
| 2017/0333664 A1 | 11/2017 | Luo et al. |
| 2018/0008791 A1 | 1/2018 | Payton et al. |
| 2018/0078721 A1 * | 3/2018 | Jalde ..................... A61B 5/285 |
| 2018/0344194 A1 * | 12/2018 | Eger ................... A61B 5/4836 |
| 2019/0070375 A1 | 3/2019 | Hacker et al. |
| 2019/0133815 A1 | 5/2019 | Nofzinger |
| 2019/0255270 A1 | 8/2019 | Larsson |
| 2019/0344005 A1 | 11/2019 | Larsson |
| 2019/0358418 A1 | 11/2019 | Sarkela et al. |
| 2020/0368464 A1 | 11/2020 | Brunetto Tancredi |
| 2021/0128852 A1 | 5/2021 | Jalde |

FOREIGN PATENT DOCUMENTS

| | | |
|---|---|---|
| CN | 106581833 A | 4/2017 |
| CN | 106821335 A | 6/2017 |
| CN | 206880920 A | 1/2018 |
| CN | 107928628 A | 4/2018 |
| EP | 1371384 A1 | 12/2003 |
| EP | 1518579 A1 | 3/2005 |
| WO | 2002078775 A2 | 10/2002 |
| WO | 2005096924 A1 | 10/2005 |
| WO | 2005107590 A1 | 11/2005 |
| WO | 2009114755 A1 | 9/2009 |
| WO | 2012085741 A1 | 6/2012 |
| WO | 2015090980 A1 | 6/2015 |
| WO | 2015138924 A1 | 9/2015 |
| WO | 2016074213 A1 | 5/2016 |
| WO | 2016079703 A1 | 5/2016 |
| WO | 2018208608 A1 | 11/2018 |
| ZA | 200502982 | 11/2005 |

OTHER PUBLICATIONS

Reilly, Charles C., et al.; "Neural respiratory drive, pulmonary mechanics and breathlessness in patients with cystic fibrosis", Thoarx 2011; pp. 240-246.

Reilly, Charles C., et al.; "Neural respiratory drive measured during inspiratory threshold loading and acute hypercapnia in healthy individuals", Experimental Physiology 2013; pp. 1190-1198.

(56) References Cited

OTHER PUBLICATIONS

Nepomuceno, V.R., et al.; "Electromyographic study on the sternocleidomastoideopectoralis major muscles during respiratory activity in humans", J. Morphol. Sci., 2014, vol. 31, No. 2; pp. 98-102.
Smith, L.L., et al.; "Neural respiratory drive measured using diaphragm and parasternal intercostal muscle electromyography during acute hypercapnia in healthy human subjects", Physiology 2014 (London, UK) (2014) Proc Physiol Soc 31, PCB144; pgs.
Estrada, Luis, et al.; "Onset and offset estimation of the neural inspiratory time in surface diaphragm electromyography: A pilot study in healthy subjects", IEEE Journal of Biomedical and Health Informatics 2016; pp. 2168-2194.
Peper, Erik, et al.; "Abdominal SEMG feedback for diaphragmatic breathing: A methodological note", Biofeedback, vol. 44, Issue 1; pp. 42-49.
Duiverman, Marieke L., et al.; "Respiratory muscle activity and patient-ventilator asynchrony during different settings of noninvasive ventilation in stable hypercapnic COPD: does high inspiratory pressure lead to respiratory muscle unloading?", International Journal of COPD 2017; pp. 243-257.
Ortega, Isabel Cristina Munoz, et al.; "Assessment of weaning indexes based on diaphragm activity in mechanically ventilated subjects after cardiovascular surgery. A pilot study", Rev Bras Ter Intensive 2017; pp. 213-221.
Koopman, Alette A., et al.; "Transcutaneous electromyographic respiratory muscle recordings to quantify patient-ventilator interaction in mechanically ventilated children", Ann Intensive Care 2018, pp. 1-9.
Lozano-Garcia, Manuel, et al.; "Surface mechanomyography and electromyography provide non-invasive indices of inspiratory muscle force and activation in healthy subjects", Scientific Reports 2018; pp. 1-14.
Bockelmann, Niclas, et al.; "Deep learning for prediction of diaphragm activity from the surface electromyogram", Current Directions in Biomedical Engineering 2019; pp. 17-20.
Buchner, Herbert, et al.; "Convolutive blind source separation on surface EMG signals for respiratory diagnostics and medical ventilation control", Cambridge University, Dept Engineering, 2019; pp. 1-5.
Dacha, Sauwaluk, et al.; "Comparison between manual and (semi-)automated analyses of esophageal diagphragm electromyography during endurance cycling in patients with COPD", Frontiers in Physiology 2019, vol. 10, Art 885; pp. 1-17.
Munoz, Isabel Cristina, et al.; "Estimation of work of breathing from respiratory muscle activity in spontaneous ventilation: A pilot study", Applied Sciences 2019; pp. 1-18.
Sarlabous, Leonardo, et al.; "Electromyography-based respiratory onset detection in COPD patients on non-invasive mechanical ventilation", Entrohy 2019, 21, 258; pp. 1-15.
Hunt, Katie A., et al.; "Prediction of extubation success using the diaphragmatic electromyograph results in ventilated neonates", J. Perinat. Med. 2020 48(5); pp. 609-614.
Clinical Trials Identifier: NCT04211038; "Assessment of Neural Inspiratory Time Through sEMG and EMGdi"; downloaded May 11, 2022; pp. 1-7.
Clinical Trials Identifier: NCT03240640; "Effects of Inspiratory Muscle Training on Shortness of Breath (Dyspnea) and Postural Control in Patients with COPD", downloaded May 11, 2022; pp. 1-15.
Clinical Trials Identifier: NCT02878993; "Predicting Infant Extubation Using Diaphragm Surface Electromyography (EMG)"; downloaded May 11, 2022; pp. 1-6.
Clinical Trials Identifier: NCT03082924; "Surface EMGdi Evaluate the Efficacy of Pulmonary Rehabilitation in Patients with COPD: a Multi Center Prospective Study"; downloaded May 11, 2022; pp. 1-9.
Netherlands Trial Register: NL4615(NTR4766); "Measuring Electrical Activity of the Diaphragm of ICU"; downloaded May 11, 2022; pp. 1-5.

\* cited by examiner

SYSTEM AND METHOD FOR PATIENT-VENTILATOR SYNCHRONIZATION/ONSET DETECTION UTILIZING TIME-FREQUENCY ANALYSIS OF EMG SIGNALS

BACKGROUND

The subject matter disclosed herein relates to control of a ventilator.

The basic modes of ventilator operation can be divided into sub-categories based on whether a ventilator or a patient initiates a breath. Patient initiated breaths are referred to as spontaneous breaths. When a ventilatory action is triggered by a spontaneous breathing event, it is of the utmost importance that the ventilator starts the inhalation process as soon as the patient tries to breathe. In other words, there should be timing synchrony between the patient effort and the ventilator action. It is estimated that in approximately 50 percent of the breaths there is patient-ventilator asynchrony. Any patient-ventilator asynchrony can lead to patient discomfort, sleep disorders, and delay the weaning of the patient. Currently, there is a delay (e.g., a few hundreds of milliseconds delay) between when the diaphragm of the patient starts muscle activation to when it leads to a change in pressure and flow at the facial region. Thus, there is a need to detect the start of inhalation effort by the patient earlier and to improve the synchronization between the patient and the ventilator during spontaneous breaths.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a computer-implemented method for detecting onset of a spontaneous breath by a patient coupled to a ventilation system is provided. The method includes receiving, at a processor, an electromyography (EMG) signal from an EMG sensor disposed on the patient. The method also includes pre-conditioning, via the processor, the EMG signal to separate the EMG signal into a plurality of components having EMG information utilizing a set of bandpass filters. The method further includes individually analyzing, via the processor, each component of the plurality of components to detect an onset of the spontaneous breath by the patient. The method still further includes determining, via the processor, the onset of the spontaneous breath by the patient is occurring when at least two components of the plurality of components indicate the onset of the spontaneous breath by the patient.

In another embodiment, a ventilation system is provided. The ventilation system includes a memory encoding processor-executable routines. The ventilation system also includes a processor configured to access the memory and to execute the processor-executable routines, wherein the routines, when executed by the processor, cause the processor to perform actions. The actions include receiving an electromyography (EMG) signal from an EMG sensor disposed on the patient. The actions also include pre-conditioning the EMG signal to separate the EMG signal into a plurality of components having EMG information utilizing a set of bandpass filters. The actions further include individually analyzing each component of the plurality of components to detect an onset of the spontaneous breath by the patient. The actions still further include determining the onset of the spontaneous breath by the patient is occurring when at least two components of the plurality of components indicate the onset of the spontaneous breath by the patient.

In a further embodiment, a non-transitory computer-readable medium is provided. The computer-readable medium includes processor-executable code that when executed by a processor, causes the processor to perform actions. The actions include receiving an electromyography (EMG) signal from an EMG sensor disposed on the patient. The actions also include pre-conditioning the EMG signal to separate the EMG signal into a plurality of components having EMG information utilizing a set of bandpass filters. The actions further include individually analyzing each component of the plurality of components to detect an onset of the spontaneous breath by the patient. The actions still further include determining the onset of the spontaneous breath by the patient is occurring when at least two components of the plurality of components indicate the onset of the spontaneous breath by the patient.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As may be appreciated, implementations of the present disclosure may be embodied as a system, method, device, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer-readable program code embodied thereon.

The present disclosure provides systems and methods for detecting the onset of spontaneous breath of a patient coupled to a ventilation system (e.g., mechanical ventilator). The disclosed embodiments utilize signals with rich frequency content (e.g., electromyography (EMG) signals) to detect the onset of spontaneous breath by the patient. In particular, the disclosed embodiments utilize online time-frequency analysis of EMG signals. Online time-frequency analysis is utilized to split the signal into multiple components carrying frequency sub-bands of the original signal. Useful components of the signal are identified and a combination of onsets detected (e.g., in two or more identified components) from each of the identified components may be utilized to obtain or detect an onset trigger (i.e., detect the onset of the spontaneous breath) to trigger providing spontaneous breathing support. In certain embodiments, triggering providing spontaneous breathing support may occur upon detecting an onset in one of the identified components and also detecting the onset of spontaneous breath utilizing a different onset detection algorithm. The disclosed embodiments may provide for faster and more accurate detection of a patient's effort to breathe. In addition, the disclosed embodiments may improve the synchronization between the ventilator and the patient.

The disclosed techniques are discussed with regard to an EMG signal. However, all or some of the disclosed techniques may be utilized on other non-stationary signals with rich frequency content to determine an onset of a spontaneous breath by a patient coupled to a ventilation system.

Figure 1:
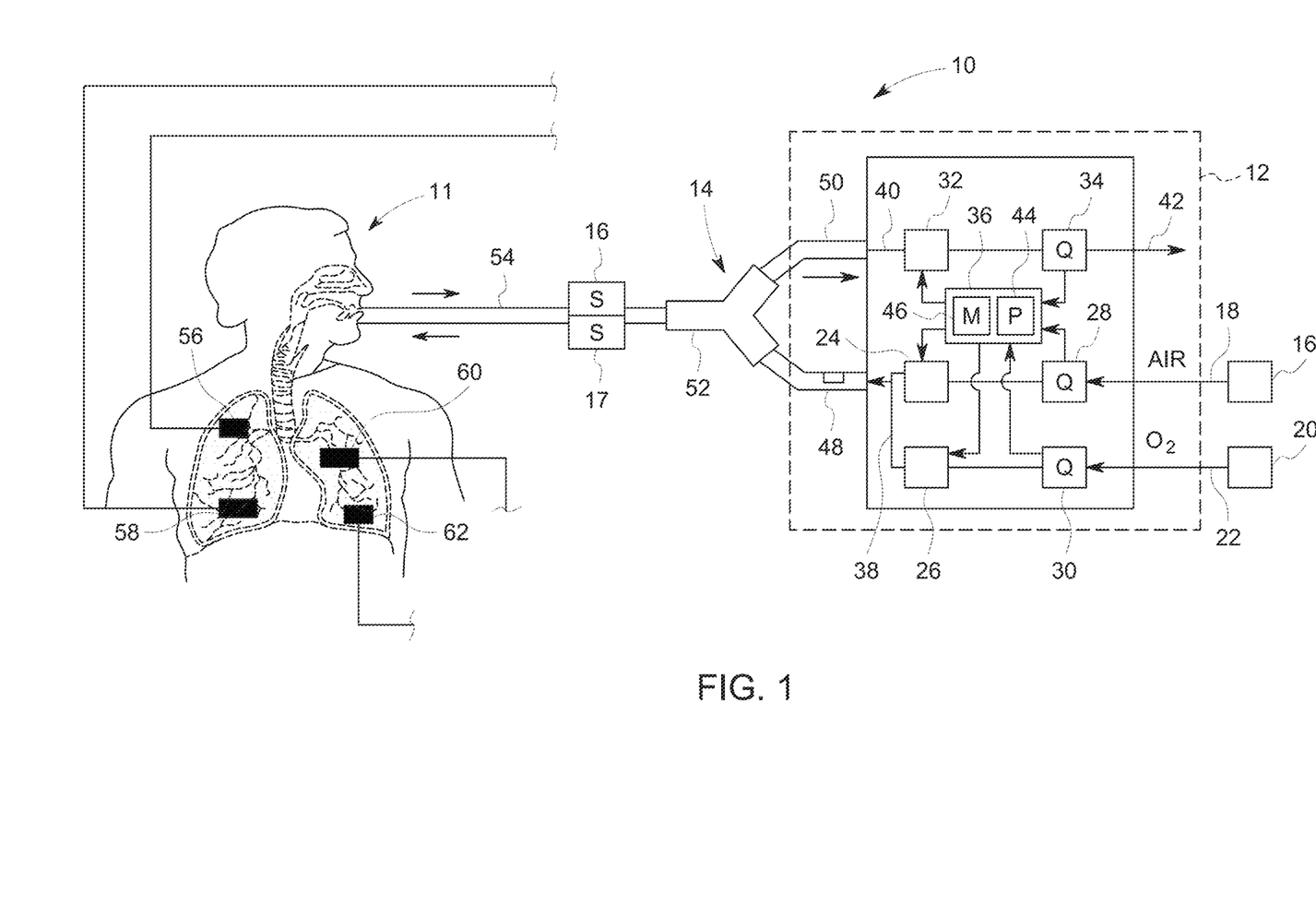
FIG. 1 is a schematic diagram of a mechanical ventilation system, in accordance with aspects of the present disclosure.

FIG. 1 schematically illustrates an example of a mechanical ventilation system 10. Ventilation system 10 provides a pneumatic circuit that carries breathing gas to and exhaled air from a patient 11 to assist patient 11 in breathing. As described in greater detail below, the ventilation system is configured to detect the onset of spontaneous breath by the patient 11 in a faster and more accurate manner than typical ventilation systems. Ventilation system 10 includes ventilator 12, breathing circuit 14, and sensors 16, 17. The ventilator 12 may operate in a number of modes. The modes include a controlled mode (with the breath is initiated by the ventilator 12), a spontaneous mode (where the breath is initiated by the patient), and a supported mode (where the breath is initiated by both the ventilator and patient). Both the spontaneous mode and the supported mode require synchronization with patient effort.

Ventilator 12 supplies gas, such as air or air including anesthetics, drugs or the like, to patient 11 through breathing circuit 14 and receives exhaled air through breathing circuit 14. In the example illustrated, ventilator 12 receives air from air source 16 through conduit 18 and receives oxygen ($O_2$) from an oxygen source 20 (such as a container of compressed oxygen) through conduit 22. The ventilator 12 includes valves 24, 26, sensors 28, 30, valve 32 and sensor 34 and controller or processing unit 36. Valves 24, 26 control a supply of air and oxygen (the mixture thereof), respectively, through conduit 38 to breathing circuit 14. Sensors 28 and 30 sense or detect the supply of the air and oxygen, respectively, and transmit signals representing such sensed values to processing unit 36.

Valve 32 includes a valve mechanism connected to breathing circuit 14 by conduit 40 so as to control the flow of exhaled air received from breathing circuit 14 to the discharge conduit 42. Sensor 34 includes a device to sense the flow of exhaled air to discharge port 42. Such sensed values for the exhaled air are further transmitted to controller or processing unit 36.

Controller 36 generates control signals controlling the operation of valves 24, 26, and 28. The controller 36 includes one or more processors 44 and a memory 46. The one or more processors 44 executes instructions contained in the memory 46. Execution of the instructions causes the controller 36 to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, the processors 44 may be embodied as part of one or more application-specific integrated circuits (ASICs). Unless otherwise specifically noted, the controller 36 is not limited to any specific combination of hardware circuitry and software, nor to any particular source for the instructions executed by the processing unit. In other implementations.

Breathing circuit 14 delivers breathing gas (air, oxygen and possibly other additives such as anesthetics, medicines and the like) from ventilator 12 to patient 11 while also directing exhaled air from patient 11 to system 10 and ventilator 12. Breathing circuit 14 includes inspiratory section or segment 48, expiration segment 50, Y connector 52 and patient segment 54. Inspiratory segment 48 extends from and is pneumatically connected to conduit 38 at one end and Y connector 52 at the other end. Segment 48 delivers gases from conduit 38 to patient segment 54 during forced, assisted or voluntary inhalation by patient 11. Exhalation segment 50 delivers exhaled gases are exhaled air from patient segment 54 to conduit 40. Y connector 52 connects each of segments 48 and 50 to patient segment 54. Patient segment 54 extends from Y connector 52 to patient 11. Patient segment 54 may include devices for pneumatically connecting with patient 11 such as through the nose, mouth or trachea of patient 11.

During inspiration (inhalation), breathing air is delivered through patient segment 54 and into the lungs of patient 11. During expiration or exhalation, expired or exhaled breathing air exits the lungs the patient 11 and is received into patient segment 54. The expired breathing air is communicated or transmitted through patient segment 54, through Y connector 52 and into expiration segment 50. Although not illustrated, in other implementations, ventilation system 10 may include additional devices or systems. For example, in one implementation, system 10 may additionally include a nebulizer positioned between ventilator 12 and inspiratory section 48 to introduce a medical drug or anesthetic agent to breathing air for the patient. In yet other implementations, breathing circuit 14 may include a component such as a humidifier to humidify the breathing air, a heater to heat the breathing air or a water/vapor trap to remove excess moisture from a particular segment or section of ventilation system 10.

In some implementations, ventilator 12 may additionally include a carbon dioxide scavenger which removes carbon dioxide from exhaled air and returns or recycles the air by conducting such recycled air to conduit 18. In one implementation, ventilator 12 utilizes a bellows to pressurize air being supplied to conduit 48. For example, in one implementation, ventilator 12 selectively supplies and withdraws pressurized air to and from an exterior of a bellows assembly. During inhalation, ventilator 12 supplies gas or air to the exterior of the bellows, collapsing the bellows to force gas within bellows to through the carbon dioxide scavenger and to the breathing circuit 14 and the patient's lungs. During exhalation, expelled gas from the patient's lungs passes through valve 32 to fill the bellows. In other implementations, the noted carbon dioxide scavenger as well as the bellows may be omitted.

The ventilation system 10 includes a number of noninvasive sensors to be utilized in determining the onset of a breath (e.g., spontaneous breath) of the patient 11. In certain embodiments, some of the sensors may be invasive (e.g., EMG sensor on a catheter passed through the mouth). Sensor 16 includes a flow sensor to measure flow and direction of gas or air within a passage (e.g., the patient segment 54). Sensor 17 includes a pressure sensor to measure flow within a passage (e.g., the patient segment 54). In certain embodiments, sensors 16, 17 are part of a device configured to sense or detect pressure and/or flow of air (with or without additives) corresponding to forced, voluntary or assisted inhalation and exhalation by patient 11. In the example illustrated, sensor 16 is located within patient segment 54. In other implementations, sensor 16 may be provided at other locations. For example, in other implementations, sensor 16 may be provided as part of a mouthpiece through which patient 11 inhales and exhales. Sensors 16 and 17 provide signals (e.g., flow and pressure signals) to provide feedback to the controller 36.

The ventilation system 10 includes an EMG sensor 56 (e.g., an EMG patch or surface sensor) disposed on the skin of patient 11 in a location adjacent the upper airway muscles. The EMG sensor 56 measures the action potentials of the respiratory muscle. The EMG sensor 56 provides an EMG signal to the controller 36. The ventilation system 10 also includes an EMG sensor 58 (e.g., an EMG patch or surface sensor) disposed on the skin of patient 11 adjacent the intercostal space. The EMG sensor 58 measures the movement of thoracic/abdominal cavity and/or diaphragm. The EMG sensor 58 provides an EMG signal to the controller 58. In certain embodiments, an EMG sensor may be placed on the skin on the rear neck region adjacent the posterior cricoarytenoid set of muscles. In certain embodiments, an EMG sensor may be invasive (e.g., via a catheter passed through the mouth). In certain embodiments, the ventilation system 10 includes one or more ECG sensors 60 disposed on the skin of the patient (e.g., in the chest region and/or intercostal space). The ECG sensor 60 measures cardiac electrical activity. The ECG sensor 60 provides the ECG signal to the controller 58. In certain embodiments, the ventilation system 10 includes one or more additional sensors 62 (e.g., ultrasound, piezoelectric, and/or inductance sensors) disposed on the skin of the patient in the chest or intercostal space. The sensors 62 measure the movement of the thoracic/abdominal cavity and/or the diaphragm. The sensors 62 provides signals to the controller 36. The sensors may be connected to the controller 36 via a wired or wireless connection. The measurements from the sensors are synchronized.

Figure 2:
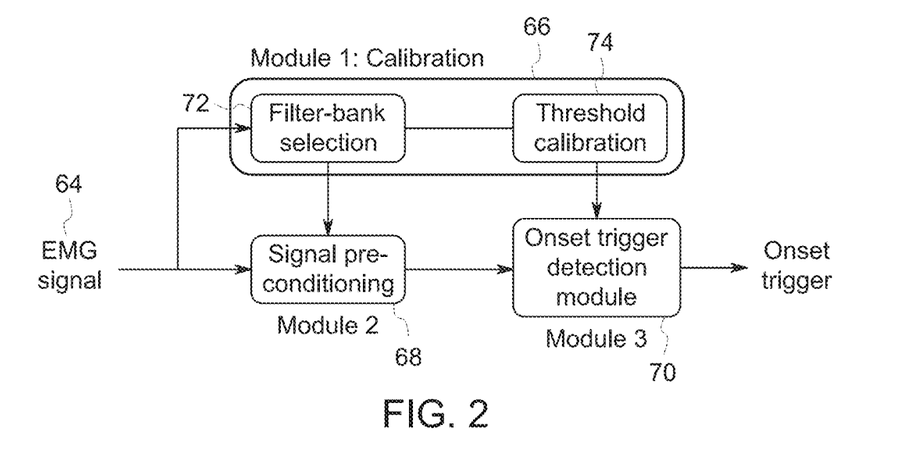
FIG. 2 is a schematic diagram of the processing of an EMG signal to determine an onset of a spontaneous breath of a patient coupled to a ventilation system, in accordance with aspects of the present disclosure.

FIG. 2 is a schematic diagram of the processing of an EMG signal 64 (e.g., raw EMG signal) to determine an onset of a spontaneous breath of a patient coupled to a ventilation system (e.g., ventilation system 10 in FIG. 1). The processing of the EMG signal 64 to determine the onset of a spontaneous breath of the patient may occur via a number of modules (e.g., stored in and executed by a processing or computing device such as controller 36 in FIG. 1). The modules include a calibration module 66, a signal pre-conditioning module 68, and an onset trigger detection module 70.

The calibration module 66 is configured to select filters (e.g., bandpass filters) from a filter bank (as indicated by block 72) to apply to the EMG signal 64 to break the signal 64 into components having useful frequency sub-bands (i.e., having significant EMG information). The calibration module 66 is also configured to determine or calibrate thresholds (as indicated by block 74) for each component (e.g., having significant EMG information) of the EMG signal 64.

The signal pre-conditioning module 68 is configured to separate the EMG signal 64 into multiple components utilizing a set of bandpass filters selected by the calibration module 66. In addition, the signal pre-conditioning module 68 is configured to identify the occurrences of ECG activity and other motion artifacts (e.g., due to body movement) in the EMG signal 64.

The onset trigger detection module 70 is configured to detect the onset of a spontaneous breath by a patient by individually analyzing each component (e.g., having significant EMG information) for the onset of the spontaneous breath utilizing the thresholds determined or calibrated for each component by the calibration module 66. The onset trigger detection module 70 is also configured to determine that the onset of the spontaneous breath by the patient is occurring when analysis of two or more (e.g., 2, 3, 4, etc.) of the components indicate onset of the spontaneous breath. In certain embodiments, the onset trigger detection module 70 is also configured to determine that the onset of the spontaneous breath by the patient is occurring when analysis of one of components indicates onset of the spontaneous breath in combination with a different onset detection algorithm detecting the onset of the spontaneous breath. The determination that the onset of the spontaneous breath is occurring results in an onset trigger 76 where a signal is provided to the ventilation system to provide breathing support to synchronize the breathing support with the onset of the spontaneous breath.

Figure 3:
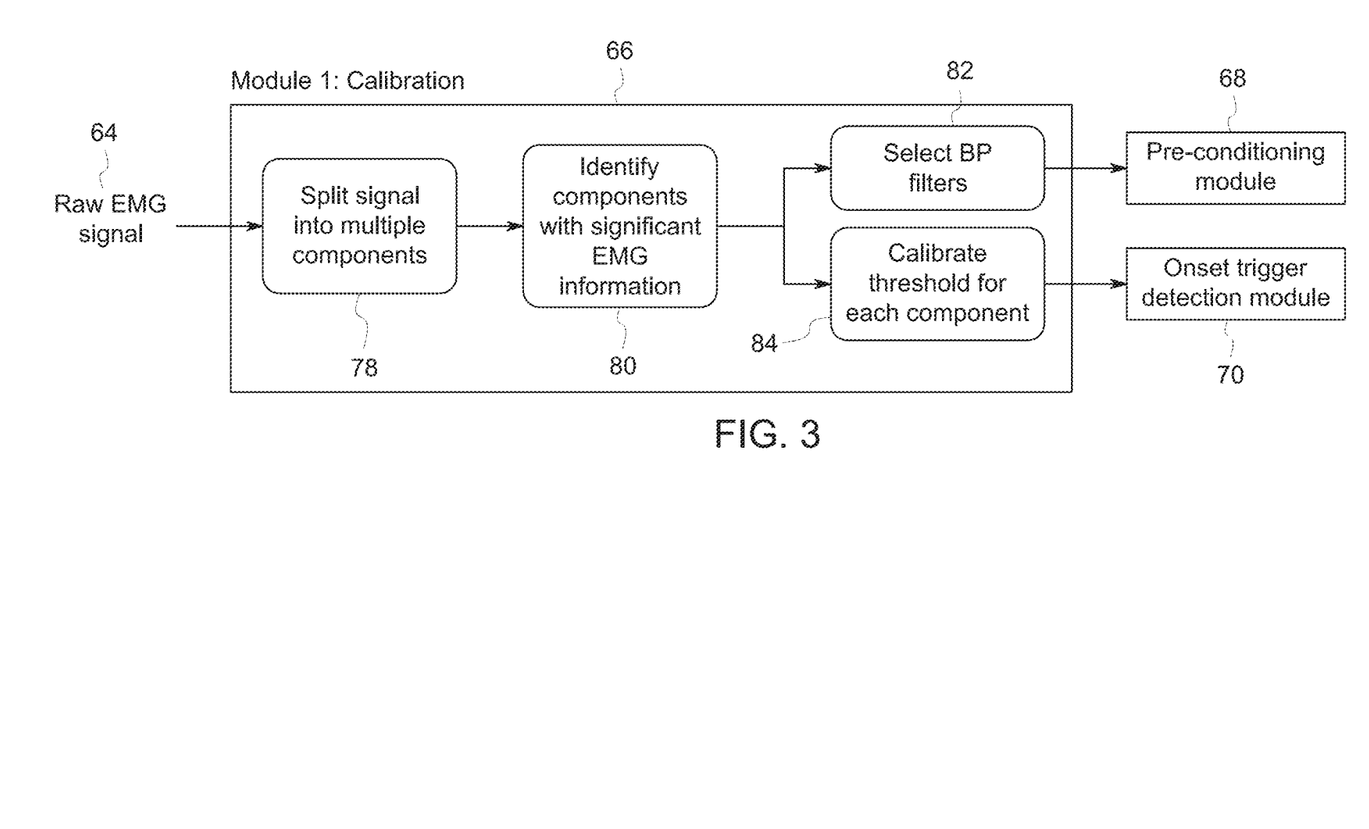
FIG. 3 is a schematic diagram of the calibration process for an EMG signal utilizing a calibration module, in accordance with aspects of the present disclosure.

FIG. 3 is a schematic diagram of the calibration process for the EMG signal 64 (e.g., raw EMG signal) utilizing the calibration module 66. The calibration module 66 is run once initially and may run again at pre-scheduled intervals (e.g., to update the bandpass filter selection and/or thresholds). The calibration module 66 receives the EMG signal 64 and separates or splits the EMG signal 64 into multiple components or levels utilizing a filter bank (block 78). For example, time-frequency analysis may be utilized via application of a discrete wavelet transform (DWT) to decompose the EMG signal 64 into multiple components. The calibration module 66 then identifies those components with significant or important EMG information (block 80). Identification of the components having significant information (e.g., useful frequency bands) may be identified by looking in each level for correlations between EMG activity and a breathing signature of the patient (e.g., obtained from a pressure sensor and/or a flow sensor of the ventilation system). Low frequency components containing ECG spikes and other motion artifacts (e.g., due to body movement) are ignored. Once the components with significant EMG information are identified, the calibration module 66 selects bandpass filters from a filter bank (block 82) that may be utilized by the signal pre-conditioning module 68 to separate the EMG signal into multiple components (e.g., having significant EMG information) in real-time. Once the components with significant EMG are identified, the calibration module 66 also determines or calibrates a threshold for each identified component (e.g., having significant EMG information) (block 84). The thresholds may be determined utilizing statistical methods and/or a dynamic threshold method.

Figure 4A:
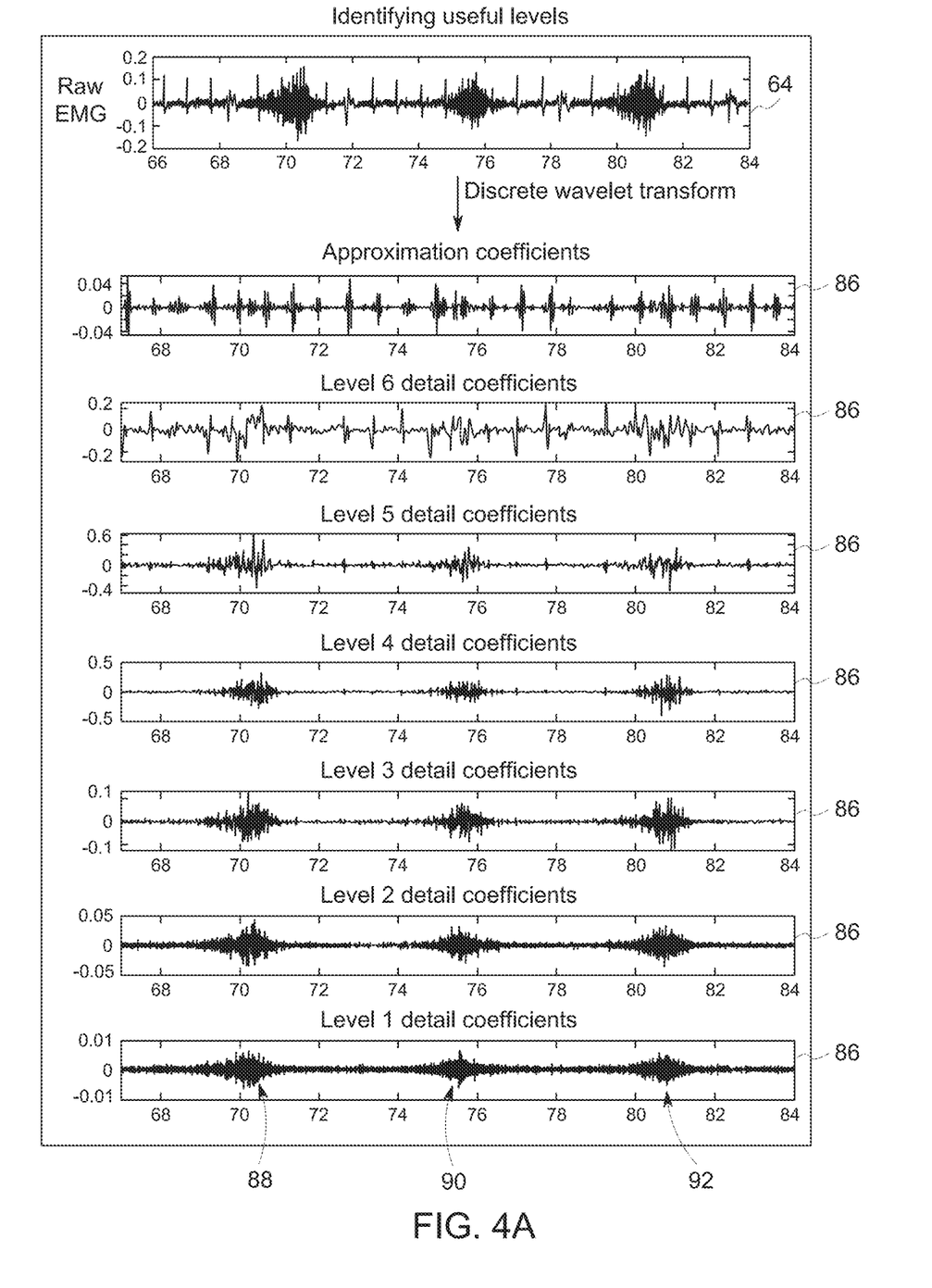
FIGS. 4A and 4B are a schematic diagram illustrating the identification of useful components of an EMG signal and the pre-conditioning of the EMG signal, in accordance with aspects of the present disclosure.
Figure 4B:
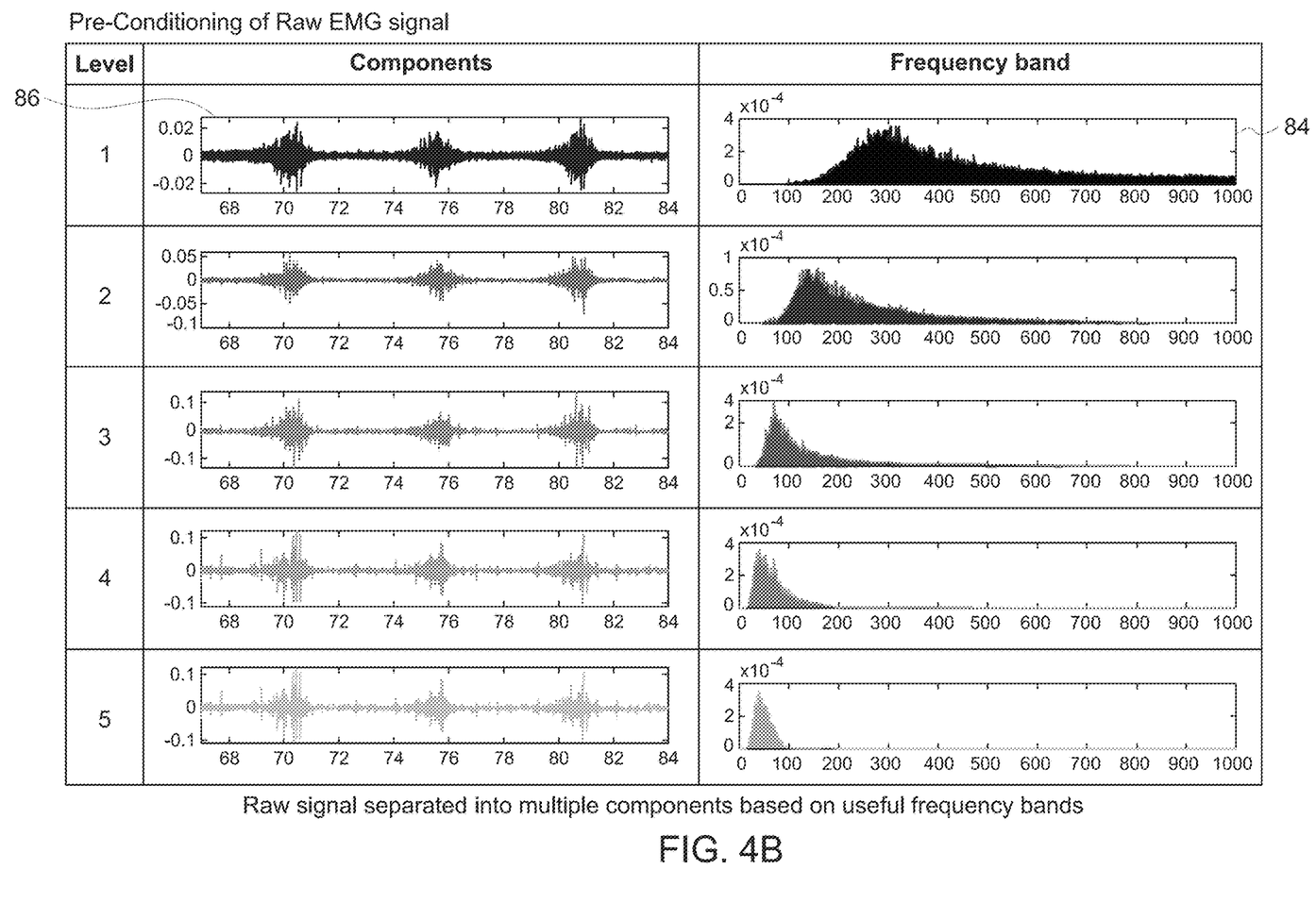

FIGS. 4A and 4B schematically illustrate the identification of useful components of the EMG signal 64 (e.g., raw EMG signal) and the pre-conditioning of the EMG signal 64. As depicted in FIG. 4A, DWT is applied to the raw EMG signal 64 resulting in decomposing the EMG signal 64 into different components or levels 86. Those components or levels having significant EMG information may be identified by looking in each level 86 for correlations between EMG activity and a breathing signature of the patient. For examples, levels 1-5 in FIG. 4A are determined to have significant EMG information (e.g., as indicated by regions 88, 90, 92 in each component 86). Low frequency components (e.g., level 6 and approximation coefficients) containing ECG spikes are ignored in selecting the bandpass filters to be utilized in pre-conditioning the EMG signal (i.e., separating the EMG signal into the identified components that include useful frequency bands). The components 86 (e.g., levels 1-5) of the EMG signal 64 having significant interest after applying the set of band pass filters and their associated frequency bands 94 are depicted in FIG. 4B.

Figure 5:
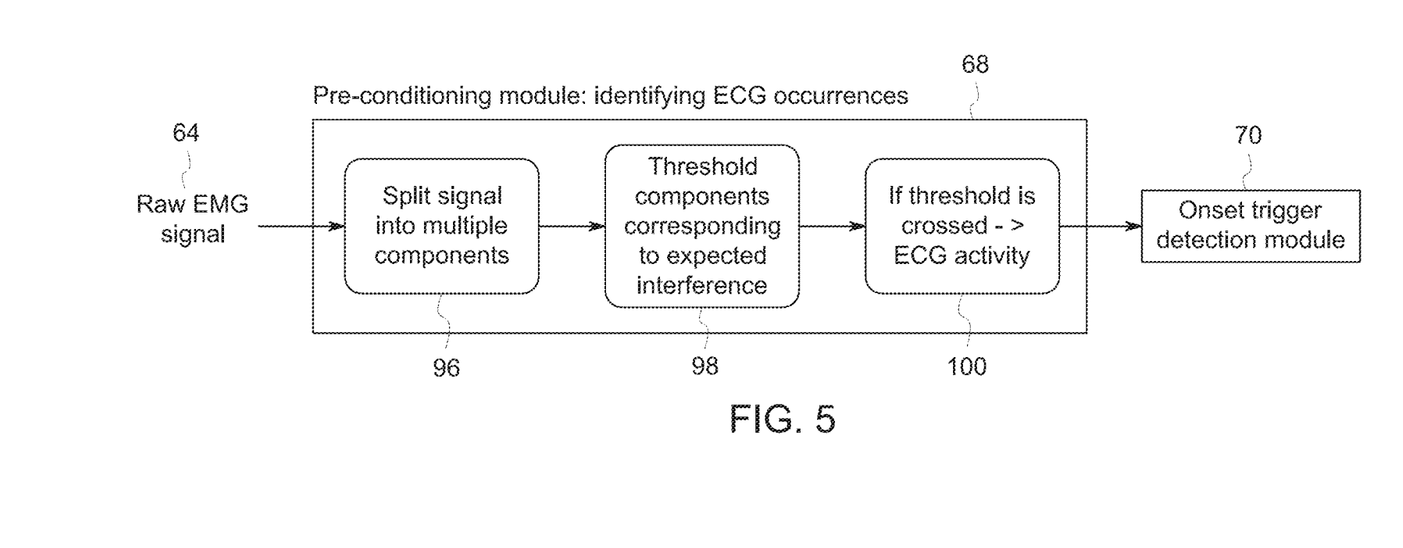
FIG. 5 is a schematic diagram of the pre-conditioning process for an EMG signal utilizing a signal pre-conditioning module to identify electrocardiogram (ECG) occurrences, in accordance with aspects of the present disclosure.

Besides separating the signal into multiple frequency components, the signal pre-conditioning module 68 is utilized to identify the occurrences of ECG activity in the EMG signal 64. FIG. 5 is a schematic diagram of the signal pre-conditioning process for the EMG signal 64 utilizing the pre-conditioning module 68 to identify ECG occurrences. The signal pre-conditioning module 68 receives the raw EMG signal 64 and splits or separates it into multiple components (block 96) utilizing a filter bank (e.g., DWT filter bank). The signal pre-conditioning module 68 then thresholds the components (i.e., compares to a threshold) corresponding to expected interference (block 98). The signal pre-conditioning module 68 detect occurrences of ECG activity if the component exceeds the threshold (block 100). The occurrences of ECG activity in the EMG signal 64 are provided to the onset trigger detection module 70 to utilize in ignoring false triggers due to residual ECG activity in the analysis of each component of the plurality of components in detecting an onset of the spontaneous breath by the patient.

Figure 6:
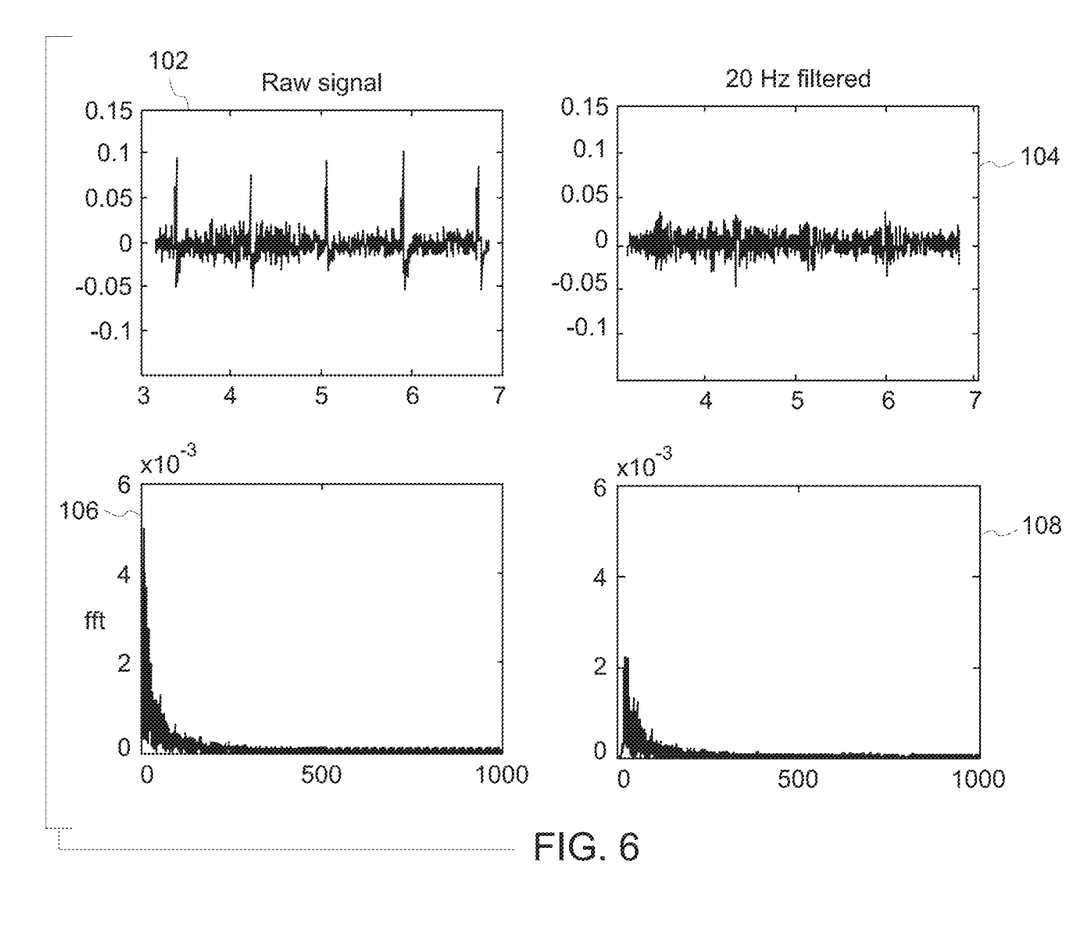
FIG. 6 illustrates plots of a raw EMG signal and a filtered EMG signal and respective fast Fourier transforms (FFT) of the raw EMG signal and the filtered EMG signal, in accordance with aspects of the present disclosure.

FIG. 6 illustrates plots of a raw EMG signal and a filtered EMG signal and respective fast Fourier transforms (FFT) of the raw EMG signal and the filtered EMG signal. Plots 102 and 104 are of the raw EMG signal 64 and a filtered EMG signal (e.g., 20 Hz filtered), respectively. Plots 106 and 108 are the fast Fourier transforms of the raw EMG signal and the filtered EMG signal, respectively.

Figure 7:
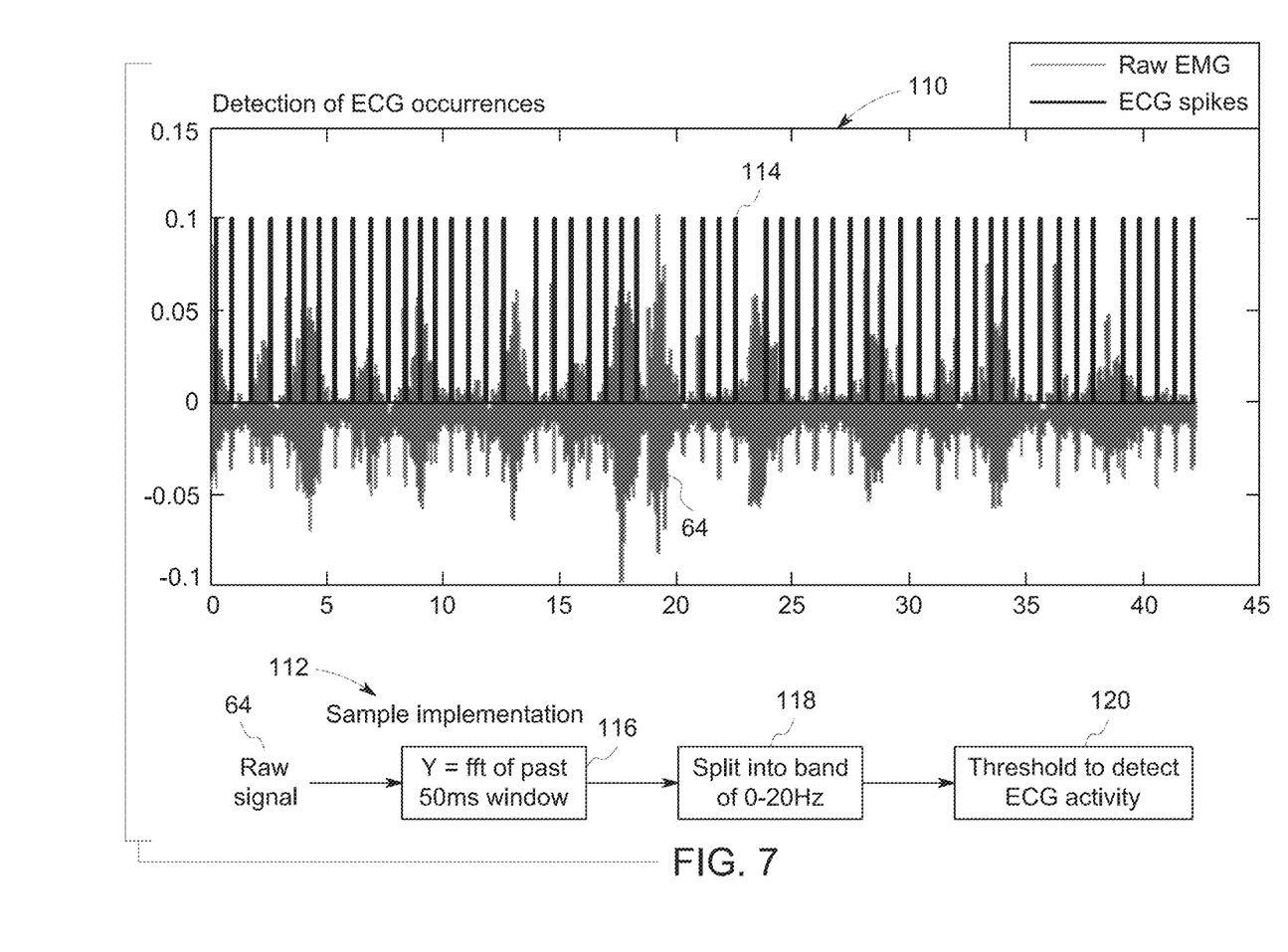
FIG. 7 illustrates a plot illustrating the detection of ECG occurrences and a process for obtaining the plot, in accordance with aspects of the present disclosure.

FIG. 7 illustrates a plot 110 illustrating the detection of ECG occurrences and a process 112 for obtaining the plot 110. The plot 110 shows ECG spikes 114 present in the raw ECG signal 64. To achieve the plot, the process 112 includes obtaining an FFT of the past 50 millisecond window of the raw EMG signal 64 (block 116). The process 112 then includes splitting (e.g. filtering) the FFT of the EMG signal 64 into a band of 0 to 20 Hz (block 118). Then thresholding to detect ECT activity is applied (block 120) to the band.

Figure 8:
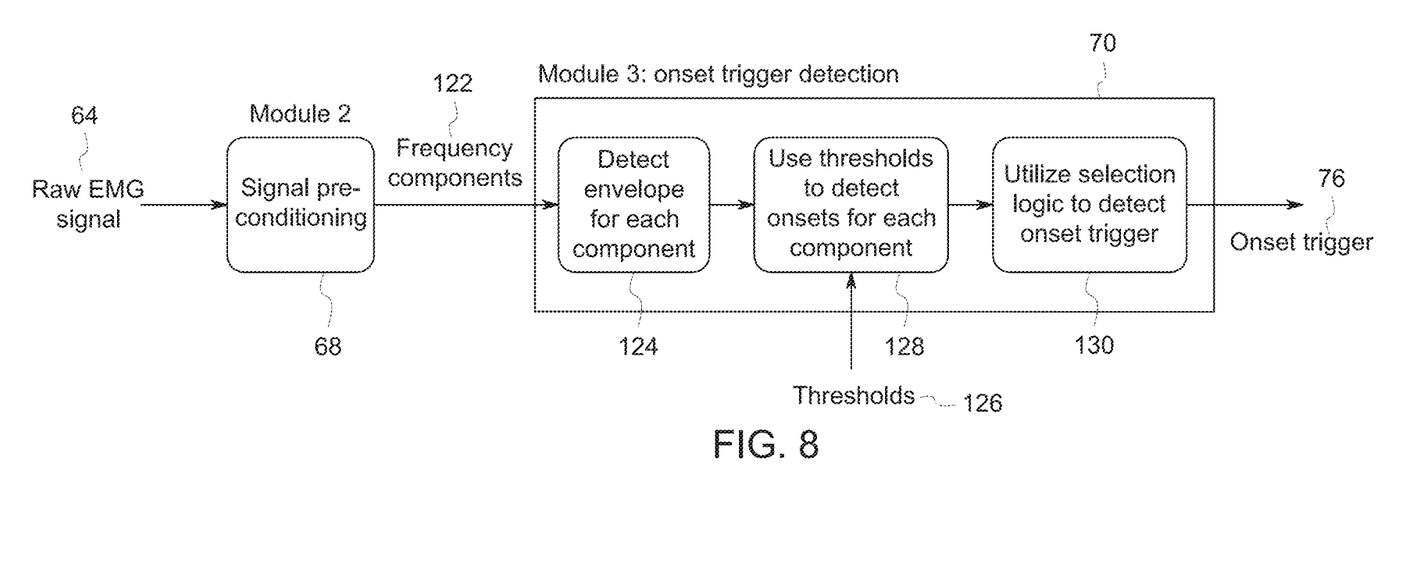
FIG. 8 is a schematic diagram of an onset trigger detection process utilizing an onset trigger detection module, in accordance with aspects of the present disclosure.

FIG. 8 is a schematic diagram of an onset trigger detection process utilizing the onset trigger detection module 70. As noted above, the signal pre-conditioning module 68 splits the raw EMG signal 64 into multiple frequency components 122 (e.g., having significant EMG information) and provides these components 122 to the onset trigger detection module 70. In certain embodiments, the signal pre-conditioning module 68 may provide ECG information (e.g., ECG occurrences) for the EMG signal 64 to the onset trigger detection module 70 to enable ignoring false triggers in detecting onset of a spontaneous breath in the patient due to residual ECG activity. The onset trigger detection module 70 detects a respective envelope for each component 122 (block 124). The onset trigger detection module 70 analyzes each component by applying respective thresholds 126 (e.g., received from the calibration module 66) to the respective envelope of each of the components 122 to detect the onset of the spontaneous breath for each component 122 (block 128). If the envelope of the component 122 surpasses the respective threshold the onset of the spontaneous breath is detected for that component 122. Finally, the onset detection module 70 utilizes a selection logic to detect the onset to determine the onset of a spontaneous breath of the patient is occurring (block 130). The selection logic details how many of the components 122 detection of the onset of the spontaneous breath must occur in before it is determined the spontaneous breath of the patient is occurring. The number of components 122 onset detection needs to occur in before determining the spontaneous breath is occurring is at least two. In certain embodiments, the number of components 122 onset detection needs to occur in may be three, four, or another number. In certain embodiments, the onset detection may need to occur in each component 122 (e.g., having significant EMG information). In certain embodiments, it may be determined that the onset of the spontaneous breath by the patient is occurring when analysis of one of components indicates onset of the spontaneous breath in combination with a different onset detection algorithm detecting the onset of the spontaneous breath. The determination that the onset of the spontaneous breath is occurring results in the onset trigger 76 (e.g., final onset trigger) where a signal is provided to the ventilation system to provide breathing support to synchronize the breathing support with the onset of the spontaneous breath.

Figure 9:
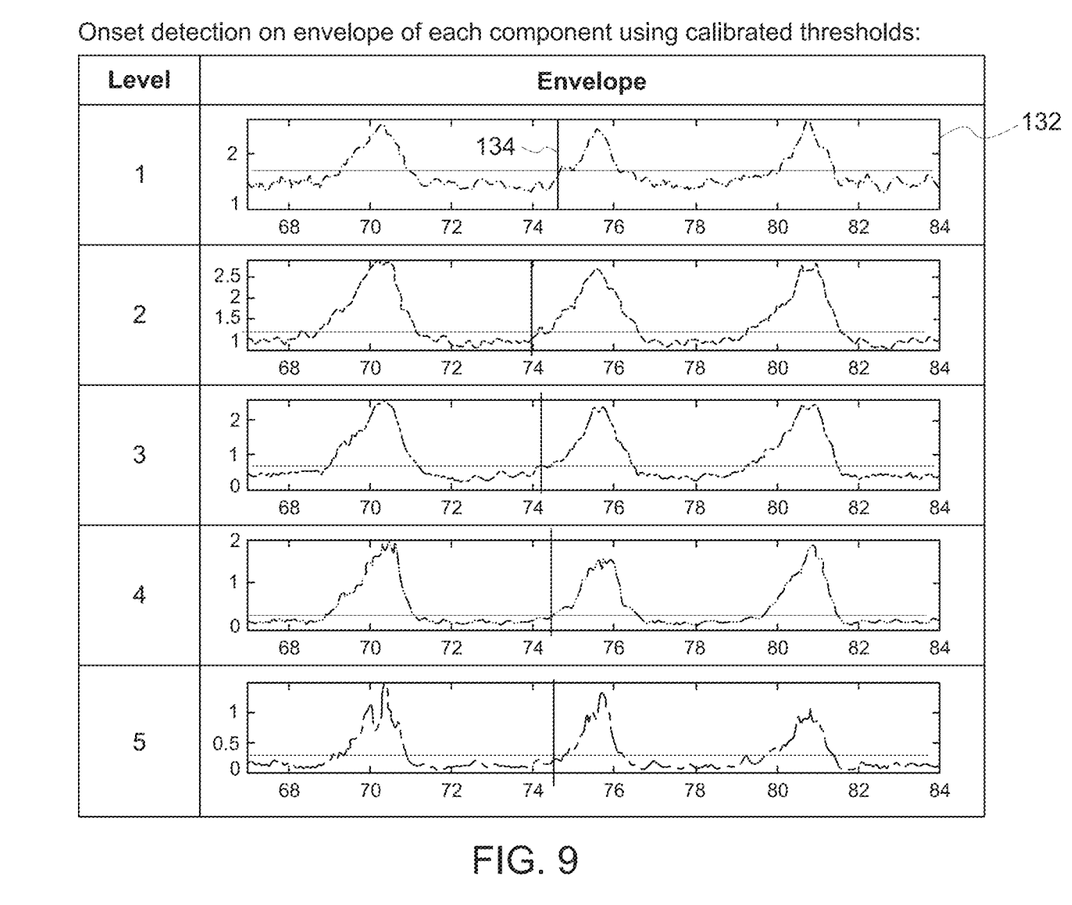
FIG. 9 illustrates utilizing calibrated thresholds for onset detection on components of an EMG signal, in accordance with aspects of the present disclosure.

FIG. 9 illustrates utilizing calibrated thresholds for onset detection on components of the EMG signal 64. FIG. 9 depicts the envelope 132 for each component (e.g., levels 1-5 in FIGS. 4A and 4B) and an indication 134 (e.g., line) along each envelope 132 where onset detection occurs by applying the respective threshold to each envelope 132. As depicted in FIG. 9, the onset detection first occurs in level 2 followed by level 3 and then rest of the levels (levels 4, 5, and 1). Once the onset detection occurs in a second level (e.g., level 3), the final onset trigger occurs.

Figure 10:
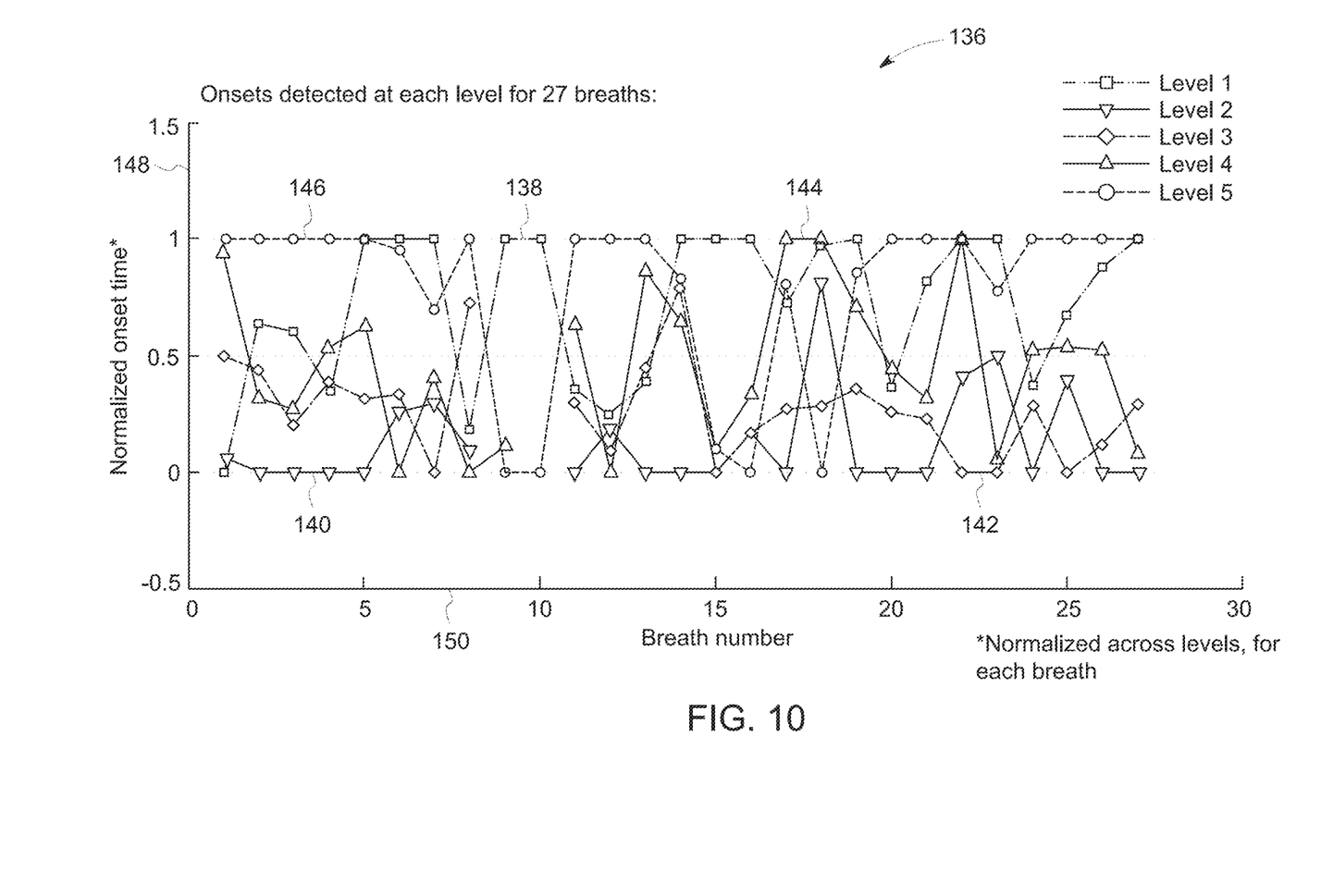
FIG. 10 illustrates the detection the relative onset time of onset of a breath for a number of breaths in multiple components of an EMG signal, in accordance with aspects of the present disclosure.

FIG. 10 illustrates the relative onset time of detection of onset of a breath for a number of breaths in multiple components of an EMG signal. Graph 136 includes plots 138, 140, 142, 144, and 146 for levels 1, 2, 3, 4, and 5, respectively, over a number of breaths (e.g., 27 breaths). The graph 136 includes a y-axis 148 representing normalized onset time (normalized across levels for each breath) and an x-axis 150 representing the breath number. As depicted in the graph 136, the onset time for each level varies from breath to breath. Utilizing a combination of the componentwise onsets enables for faster and more accurate onset detection of the occurrence of a spontaneous breath.

Technical effects of the disclosed embodiments include utilizing signals with rich frequency content (e.g., EMG signals) to detect the onset of spontaneous breath by the patient via online time-frequency analysis of EMG signals. Useful components of the EMG signal are identified and a combination of onsets detected (e.g., in two or more identified components) from each of the identified components may be utilized to obtain or detect an onset trigger (i.e., detect the onset of the spontaneous breath) to trigger providing breathing support to the patient. The disclosed embodiments may provide for faster and more accurate detection of a patient's effort to breathe. In addition, the disclosed embodiments may improve the synchronization between the ventilator and the patient.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the invention, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for detecting onset of a spontaneous breath by a patient coupled to a ventilation system, comprising:
   receiving, at a processor, an electromyography (EMG) signal from an EMG sensor disposed on the patient;
   pre-conditioning, via the processor, the EMG signal to separate the EMG signal into a plurality of components having EMG information utilizing a set of bandpass filters;
   individually analyzing, via the processor, each component of the plurality of components to detect an onset of the spontaneous breath by the patient;
   determining, via the processor, the onset of the spontaneous breath by the patient is occurring when at least two components of the plurality of components indicate the onset of the spontaneous breath by the patient; and
   providing, via the processor, a signal to trigger providing breathing support, via the ventilation system, to the patient when it is determined that the onset of the spontaneous breath is occurring to synchronize the breathing support with the onset of the spontaneous breath.

2. The method of claim 1, comprising, prior to pre-conditioning the EMG signal, identifying, via the processor, components having EMG information in the plurality of components.

3. The method of claim 2, wherein identifying the components having EMG information comprises correlating EMG activity in each component of the plurality of components with a breathing signature obtained from the patient.

4. The method of claim 2, comprising selecting, via the processor, the set of bandpass filters to utilize in pre-conditioning from a filter bank based on the identified components.

5. The method of claim 2, comprising computing, via the processor, a respective threshold for each component of the plurality of components to utilize in detecting the onset of the spontaneous breath.

6. The method of claim 5, wherein individually analyzing each component of the plurality of components to detect the onset of the spontaneous breath by the patient comprises detecting an envelope for each component of the plurality of components and comparing the envelope for each component to its respective threshold.

7. The method of claim 1, wherein pre-conditioning the EMG signal comprises identifying occurrences of ECG activity in the EMG signal for utilization in ignoring false triggers due to residual ECG activity in the analysis of each component of the plurality of components in detecting an onset of the spontaneous breath by the patient.

8. A ventilation system, comprising:
   a memory encoding processor-executable routines;
   a processor configured to access the memory and to execute the processor-executable routines, wherein the routines, when executed by the processor, cause the processor to:
      receive an electromyography (EMG) signal from an EMG sensor disposed on the patient;
      pre-condition the EMG signal to separate the EMG signal into a plurality of components having EMG information utilizing a set of bandpass filters;
      individually analyze each component of the plurality of components to detect an onset of the spontaneous breath by the patient;
      determine the onset of the spontaneous breath by the patient is occurring when at least two components of the plurality of components indicate the onset of the spontaneous breath by the patient; and
      provide a signal to trigger providing breathing support, via the ventilation system, to the patient when it is determined that the onset of the spontaneous breath is occurring to synchronize the breathing support with the onset of the spontaneous breath.

9. The ventilation system of claim 8, wherein pre-conditioning the EMG signal comprises identifying occurrences of ECG activity in the EMG signal for utilization in ignoring false triggers due to residual ECG activity in the analysis of each component of the plurality of components in detecting an onset of the spontaneous breath by the patient.

10. The ventilation system of claim 8, wherein the routines, when executed by the processor, cause the processor to, prior to pre-conditioning the EMG signal, identify components having EMG information in the plurality of components.

11. The ventilation system of claim 10, wherein identifying the components having EMG information comprises correlating EMG activity in each component of the plurality of components with a breathing signature obtained from the patient.

12. The ventilation system of claim 10, wherein the routines, when executed by the processor, cause the processor to select the set of bandpass filters to utilize in pre-conditioning from a filter bank based on the identified components.

13. The ventilation system of claim 10, wherein the routines, when executed by the processor, cause the processor to compute a respective threshold for each component of the plurality of components to utilize in detecting the onset of the spontaneous breath.

14. The ventilation system of claim 13, wherein individually analyzing each component of the plurality of components to detect the onset of the spontaneous breath by the patient comprises detecting an envelope for each component of the plurality of components and comparing the envelope for each component to its respective threshold.

15. A non-transitory computer-readable medium, the computer-readable medium comprising processor-executable code that when executed by a processor, causes the processor to:
- receive an electromyography (EMG) signal from an EMG sensor disposed on the patient;
- pre-condition the EMG signal to separate the EMG signal into a plurality of components having EMG information utilizing a set of bandpass filters;
- individually analyze each component of the plurality of components to detect an onset of the spontaneous breath by the patient;
- determine the onset of the spontaneous breath by the patient is occurring when at least two components of the plurality of components indicate the onset of the spontaneous breath by the patient; and
- provide a signal to trigger providing breathing support, via the ventilation system, to the patient when it is determined that the onset of the spontaneous breath is occurring to synchronize the breathing support with the onset of the spontaneous breath.

16. The non-transitory computer-readable medium of claim 15, wherein the processor-executable code, when executed by the processor, cause the processor to, prior to pre-conditioning the EMG signal, identify components having EMG information in the plurality of components by correlating EMG activity in each component of the plurality of components with a breathing signature obtained from the patient.

17. The non-transitory computer-readable medium of claim 16, wherein individually analyzing each component of the plurality of components to detect the onset of the spontaneous breath by the patient comprises detecting an envelope for each component of the plurality of components and comparing the envelope for each component to a respective threshold specific to each component.

* * * * *